United States Patent [19]

Takamatsu et al.

[11] Patent Number: 4,906,764
[45] Date of Patent: Mar. 6, 1990

[54] PROCESS FOR PRODUCING PHOSPHINYLAMINO ACID DERIVATIVES

[75] Inventors: Hideki Takamatsu; Hiroyuki Mutoh; Fumio Suzuki; Shinichiro Takigawa, all of Funabashi, Japan

[73] Assignee: Nissan Chemical Industries Ltd., Tokyo, Japan

[21] Appl. No.: 193,775

[22] Filed: May 13, 1988

[30] Foreign Application Priority Data

May 26, 1987 [JP] Japan .................. 62-129498
Mar. 14, 1988 [JP] Japan .................. 63-59872

[51] Int. Cl.$^4$ .................. C07F 9/30; C07F 9/32
[52] U.S. Cl. .................. 558/87; 558/174; 562/15
[58] Field of Search .......... 558/174, 87; 562/15

[56] References Cited

U.S. PATENT DOCUMENTS 3,766,266 10/1973 Nakamatsu et al. ........ 260/534 C
4,777,279 10/1988 Zeiss .................. 558/174

FOREIGN PATENT DOCUMENTS 85391 8/1983 European Pat. Off.
292918 11/1988 European Pat. Off.
2115985 10/1971 Fed. Rep. of Germany.

Primary Examiner—Anton H. Sutto
Attorney, Agent, or Firm—Oblon, Spivak, McClelland, Maier & Neustadt

[57] ABSTRACT

A process for producing a phosphinylamino acid derivative of the formula:

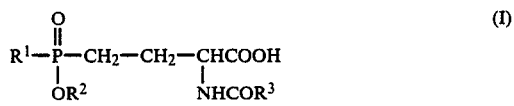

wherein $R^1$ is a lower alkyl group, $R^2$ is a hydrogen atom, a lower alkyl group, a halo-lower alkyl group or a substituted or unsubstituted phenyl group, and $R^3$ is a substituted or unsubstituted alkyl group or a substituted or unsubstituted phenyl group, which comprises reacting a compound of the formula:

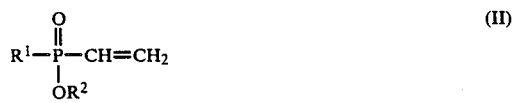

wherein $R^1$ and $R^2$ are as defined above, and/or a compound of the formula:

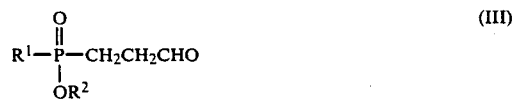

wherein $R^1$ and $R^2$ are as defined above, with a compound of the formula:

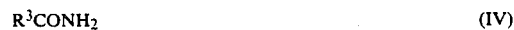

wherein $R^3$ is as defined above, carbon monoxide and hydrogen in the presence of a catalyst containing a metal of group VIII of the Periodic Table.

9 Claims, No Drawings

PROCESS FOR PRODUCING PHOSPHINYLAMINO ACID DERIVATIVES

The present invention relates to a novel process for producing phosphinylamino acid derivatives useful as intermediates for compounds useful as active ingredients of herbicides.

Heretofore, the following publications are known to disclose processes for the preparation of phosphinylamino acid derivatives:

(1) Japanese Unexamined Patent Publication No. 131993/1983
(2) Japanese Unexamined Patent Publication No. 139727/1977

The publication (1) discloses a process for the production which may be represented by the following reaction scheme:

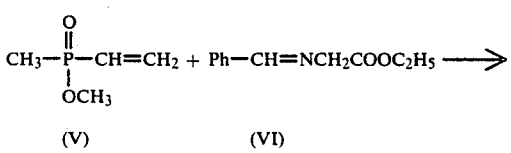

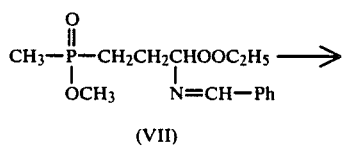

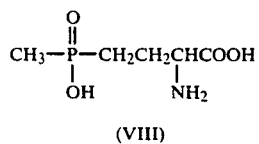

In the above reaction scheme, Ph represents a phenyl group.

The above publication (2) discloses a process for the preparation which may be represented by the following reaction scheme:

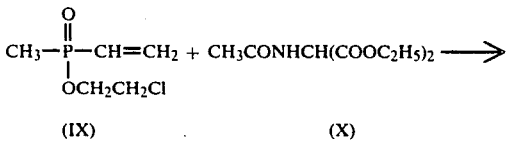

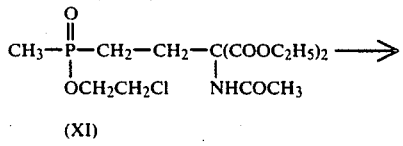

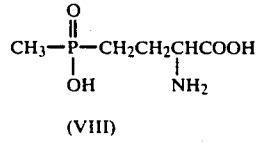

An ammonium salt of the compound of the formula VIII is an active compound of a commercially available herbicide.

In the above two processes, the reactions are conducted under atmospheric pressure, and compounds of the formula VIII are prepared via intermediates of the formula VII and XI, respectively. However, compounds of the formula VI and X used as starting materials, are considerably expensive, and the processes are not advantageous from the practical industrial point of view.

On the other hand, Japanese Examined Patent Publication No. 17259/1973 discloses a process which may be represented by the following reaction scheme:

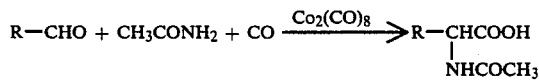

In the above reaction scheme, R is an alkyl group.

In this process, the reaction is conducted under an elevated pressure. This is a process for the preparation of a usual amino acid derivative and is not a process for the production of a phosphinylamino derivative containing a phosphorus atom as in the present invention. Besides, the yield in this reaction is low as compared with the process of the present invention.

In addition to the above prior art, U.S. Pat. Nos. 3,766,266, 4,264,515 and 4,496,756 disclose processes for the production of amino acid derivatives by utilizing a reaction for conversion to amidocarbonyl.

However, none of such processes disclose a method for separating the formed amino acid derivatives from the catalyst.

Heretofore, the following publications are known to disclose methods for separating water-soluble oxo reaction products and catalysts:

(1) Japanese Examined Patent Publication No. 17209/1962
(2) Japanese Examined Patent Publication No. 6734/1966
(3) Japanese Examined Patent Publication No. 29936/1968

The above publications (1), (2) and (3) are concerned with methods wherein a cobalt catalyst in a reaction. product is oxidized, and then the formed cobalt ions are adsorbed on a cation exchange resin, whereby water-soluble nonionic β-cyanopropionaldehyde and its dimethylacetal are separated, and they are not concerned with a method of separating an ionic amino acid derivative and metal ions.

The present inventors have conducted extensive researches for a process for industrially advantageously producing phosphinyl amino acid derivatives useful as intermediates for active compounds of herbicides and as a result, have found that by using a compound having a vinyl group directly bonded to a phosphorus atom as a starting material, the reaction for conversion to amidocarbonyl can be readily conducted with a small amount of a catalyst and in a short period of time to obtain a desired phosphinyl amino acid derivative in good yield and with a high purity. The present invention has been accomplished on the basis of this discovery.

Namely, the present invention provides a process for producing a phosphinylamino acid derivative of the formula

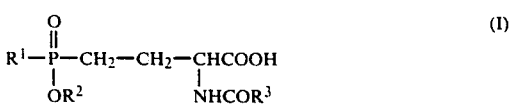

wherein $R^1$ is a lower alkyl group, $R^2$ is a hydrogen atom, a lower alkyl group, a halo-lower alkyl group or a substituted or unsubstituted phenyl group, and $R^3$ is a substituted or unsubstituted alkyl group or a substituted or unsubstituted phenyl group, which comprises reacting a compound of the formula:

$$R^1-\underset{\underset{OR^2}{|}}{\overset{\overset{O}{\|}}{P}}-CH=CH_2 \quad (II)$$

wherein $R^1$ and $R^2$ are as defined above, and/or a compound of the formula:

$$R^1-\underset{\underset{OR^2}{|}}{\overset{\overset{O}{\|}}{P}}-CH_2CH_2CHO \quad (III)$$

wherein $R^1$ and $R^2$ are as defined above, with a compound of the formula:

$$R^3CONH_2 \quad (IV)$$

wherein $R^3$ is as defined above, carbon monoxide and hydrogen in the presence of a catalyst containing a metal of Group VIII of the Periodic Table.

Further, the present invention provides a process for producing a phosphinylamino acid derivative of the formula I, which comprises reacting a compound of the formula II and/or a compound of the formula III, with a compound of the formula IV, carbon monoxide and hydrogen in the presence of a catalyst containing a metal of Group VIII of the Periodic Table, and then separating the catalyst containing a Group VIII metal from the reaction solution by oxidizing the catalyst in the reaction solution in the presence of a mineral acid and adsorbing it on a cation exchange resin.

Now, the present invention will be described in detail with reference to the preferred embodiments.

The process of the present invention may be represented by the following reaction scheme:

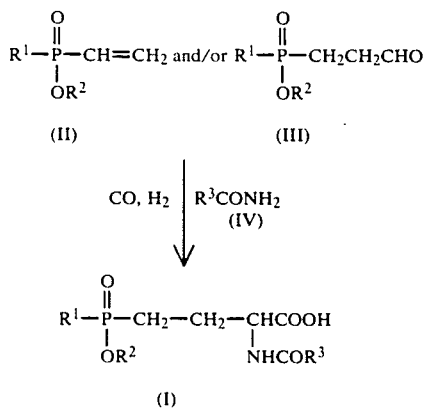

In the present invention, substituent $R^1$ is a lower alkyl group such as methyl, ethyl, n-propyl, iso-propyl, n-butyl, iso-butyl or tert-butyl. Among them, a methyl group is preferred.

Substituent $R^2$ is a hydrogen atom, a lower alkyl group such as methyl, ethyl, n-propyl, iso-propyl, n-butyl, iso-butyl or tert-butyl, a halo-lower alkyl group such as halogenomethyl, halogenoethyl, halogenopropyl or halogenobutyl, or a substituted or unsubstituted phenyl group such as phenyl or benzyl.

The halogen for the halo-lower alkyl group includes chlorine, fluorine, iodine and bromine.

The substituent for the substituted phenyl group is not particularly limited and includes, for example, lower alkyl groups and halogen atoms.

The halogen atoms include chlorine, fluorine, iodine and bromine.

Substituent $R^2$ is preferably a methyl group, a 1-chloroethyl group or a 2-chloroethyl group.

Substituent $R^3$ may be a hydrogen atom, a substituted or unsubstituted alkyl group such as methyl, ethyl, n-propyl, iso-propyl, n-butyl, iso-butyl, tert-butyl, dodecyl or chloromethyl, a substituted or unsubstituted phenyl group such as phenyl, methylphenyl, trimethylphenyl, butylphenyl, methoxyphenyl, cyanophenyl, fluorophenyl, difluorophenyl, fluorochlorophenyl, chlorophenyl, dichlorophenyl, methylchlorophenyl, bromophenyl, benzoylphenyl, methylphenylbutyl, naphthyl or benzyl, a pyridinyl group or an amino group. Among them, a methyl group and a phenyl group are preferred.

With respect to the molar ratio of the starting materials, the compound of the formula IV is used usually in an amount within a range of from 0.2 to 5 mols, preferably from 0.5 to 2 mols, per mol of the total amount of the compound of the formula II and/or the compound of the formula III.

With respect to the mixing ratio of carbon monoxide gas and hydrogen gas, carbon monoxide is used usually in an amount within a range of from 0.1 to 10 mols, preferably from 0.2 to 5 mols, per mol of hydrogen.

In the case of the compound of the formula III, the reaction may be conducted by using carbon monoxide alone.

The catalyst containing a metal of Group VIII of the Periodic Table includes catalysts containing metals such as iron, cobalt, nickel, ruthenium, rhodium, osmium, iridium and platinum. Particularly effective are their carbonyl compounds. Cobalt carbonyl compounds and rhodium carbonyl compounds are preferred.

The cobalt carbonyl compounds include, for example, hydrocobalt tetracarbonyl and dicobalt octacarbonyl.

The rhodium carbonyl compounds include tetrarhodium carbonyl and hexarhodium hexadecacarbonyl.

The catalyst may be a single compound or a mixture of the above compounds.

There is no particular restriction as to the amount of the catalyst. In the case of cobalt, the catalyst is used usually in an amount of from 0.01 to 10 g atom as cobalt metal relative to 100 mols of the total amount of the compound of the formula II and/or the compound of the formula III. An amount within a range of from 0.05 to 6 g atom is practically preferred.

In the case of rhodium, the catalyst is used usually within a range of from 0.001 to 2 g atom as rhodium metal relative to 100 mols of the total amount of the compound of the formula II and/or the compound of the formula III. An amount within a range of from 0.01 to 1 g atom is practically preferred.

A phosphine compound may be employed to stabilize the catalyst. For example, a tri-lower alkylphosphine such as trimethylphosphine, triethylphosphine or tributylphosphine, and triphenylphosphine may be mentioned. The reaction pressure in the present invention is within a range of from 10 to 400 kg/cm²G, preferably within a range of from 40 to 350 kg/cm²G, more preferably the reaction pressure is within a range of from 70 to 300 kg/cm²G.

The reaction temperature is usually from 20° to 250° C., preferably from 40° to 200° C., more preferably from 60° to 170° C.

The reaction of the present invention may proceed in the absence of a solvent. However, a solvent may be used for the reaction.

It is usually preferred to employ a solvent capable of dissolving the compound of the formula IV.

There is no particular restriction as to the solvent so long as it is an inert solvent. Useful solvents include, for example, ethers such as diether ether, tetrahydrofuran and dioxane, esters such as methyl acetate and ethyl acetate, ketones such as acetone, methyl ethyl ketone and acetophenone, aromatic hydrocarbons such as benzene, toluene and xylene and aliphatic hydrocarbons such as hexane and heptane.

There is no particular restriction in the manner for the operation of the process of the present invention. or example, it is possible to employ a method wherein the compound of the formula II and/or the compound of the formula III are charged together with the compound of the formula IV into a reactor, followed by introducing and reacting a gas mixture of carbon monoxide and hydrogen thereto to obtain a phosphinylamino acid derivative of the formula I, or a method wherein the compound of the formula II and/or the compound of the formula III are charged into a reactor, then introducing and reacting a gas mixture of carbon monoxide and hydrogen thereto, followed by adding and reacting the compound of the formula IV to obtain a phosphinylamino acid derivative of the formula I.

The method for separating the phosphinylamino acid derivative of the formula I as the reaction product of the present invention and the catalyst containing a metal of Group VIII of the Periodic Table comprises oxidizing the catalyst in the presence of a mineral acid to convert it into metal ions, which are then adsorbed on a H-type cation exchange resin for separation, to obtain the phosphinylamino acid derivative.

The mineral acid includes, for example, hydrochloric acid, sulfuric acid or nitric acid. Hydrochloric acid is preferred. There is no particular restriction as to the amount of the mineral acid, but it is used usually in an amount of at least equivalent to the catalyst.

The oxidizing agent includes, for example, an oxygen-containing gas such as air, hydrogen peroxide and chlorine. There is no particular restriction as to the amount of the oxidizing agent, but it is usually used in an equivalent amount to the catalyst.

There is no particular restriction as to the temperature for the oxidizing treatment, and the treatment may be conducted at room temperature.

The cation exchange resin is preferably of a sulfonic acid type.

There is no particular restriction as to the temperature for the cation exchange resin treatment, and the treatment may be conducted at room temperature.

The catalyst metal ions adsorbed on the cation exchange resin may be desorbed and recovered as a metal salt by a usual method.

Further, in the process of the present invention, after completion of the reaction, by-products in the reaction product may be extracted and removed by contacting the reaction product with an organic solvent in any optional step after the oxidizing treatment and the cation exchange treatment.

As such an organic solvent, an aliphatic hydrocarbon such as hexane or heptane, an aromatic hydrocarbon such as benzene or xylene, a halogenated hydrocarbon such as dichloromethane, chloroform or carbon tetrachloride or an ether compound such as dimethyl ether, diethyl ether, ethyl ether or dipropyl ether may be mentioned. Among them, benzene and toluene are preferred.

The organic solvent is used usually in an amount of from 0.1 to 100 parts by weight per one part by weight of the solution to be treated.

There is no particular restriction as to the temperature for the extraction for removal. However, the extraction is preferably conducted at a temperature lower than the boiling point of the organic solvent.

According to the process of the present invention, the phosphinylamino acid derivative of the formula I can readily be obtained in good yield with a small amount of the catalyst in a short period of time. Thus, the process is extremely advantageous from the industrial point of view.

According to the method for separating the catalyst containing a metal of Group VIII of the Periodic Table from the reaction product of the present invention, the catalyst can readily be separated, and the phosphinylamino acid derivative of the formula I can be obtained in a high purity without loss.

Further, the phosphinylamino acid derivative of the formula I can readily be converted to a compound of the formula VIII by hydrolysis:

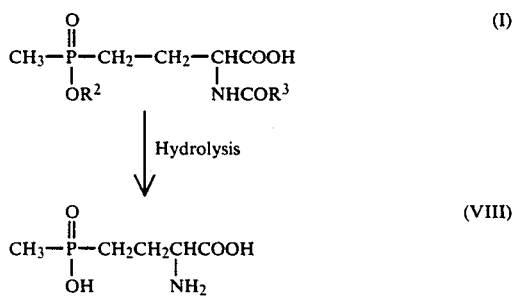

An ammonium salt of the above compound of the formula VIII is an active ingredient of a commercially available non-selective herbicide for foliage treatment (common name: Glufosinate).

Further, the phosphinylamino acid derivative of the formula I can readily be converted to a L-form of the compound of the formula VIII [L-2-amino-4-(hydroxymethylphosphinyl)butylic acid] by hydrolyzing the acyl groups by using bacteria belonging to Genus Pseudomonas, ray fungi belonging to Genus Streptomyces or moulds belonging to Genus Aspergillus and, if necessary, hydrolyzing the product with an acid:

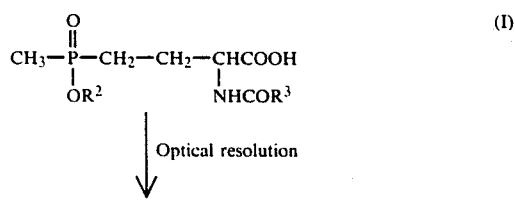

-continued $$L-CH_3-\overset{O}{\underset{OH}{\overset{\|}{P}}}-CH_2\underset{NH_2}{CHCOOH} \quad (VIII)$$

Now, the present invention will be described in further detail with reference to Examples. However, it should be understood that the present invention is by no means restricted to these specific Examples.

EXAMPLE 1

$$CH_3-\overset{O}{\underset{OCH_3}{\overset{\|}{P}}}-CH=CH_2 + CH_3CONH_2 + 2CO + H_2 \longrightarrow$$

$$CH_3-\overset{O}{\underset{OCH_3}{\overset{\|}{P}}}-CH_2CH_2\underset{NHCOCH_3}{CHCOOH}$$

Into a 100 ml stainless steel autoclave, 50 g of dioxane, 6.01 g (50 mmol) of vinylmethylphosphinic acid methyl ester, 4.43 g (75 mmol) of acetamide, 342 mg (1.0 mmol) of dicobalt octacarbonyl and 28.3 mg (0.025 mmol) of hexarhodium hexacarbonyl were charged.

The autoclave was flushed with a gas mixture of carbon monoxide and hydrogen (1:1 in molar ratio), and the reaction was conducted at 100° C. under 120 kg/cm²G for 0.5 hour and then at 120° C. for further 0.5 hour.

The autoclave was cooled, and the reaction product was taken out and analyzed by gas chromatography, whereby the conversion of the vinylmethylphosphinic acid methyl ester was 100%.

The solvent was distilled off, and the residue was repeatedly extracted with an organic solvent to obtain 11.86 g of the product.

From the proton NMR analysis, this product was found to contain 85% by weight of the desired N-acetyl-2-amino-4-methoxymethylphosphinylbutyric acid.

This product was hydrolyzed with hydrochloric acid to obtain 2-amino-4-hydroxymethylphosphinylbutyric acid hydrochloride. This hydrochloride was identified by liquid chromatography analysis to be the same as the standard 2-amino-4-hydroxymethylphosphinylbutyric acid hydrochloride.

Further, this hydrochloride was converted to an ammonium salt, which was identified in a similar manner.

EXAMPLE 2

$$CH_3-\overset{O}{\underset{OCH_3}{\overset{\|}{P}}}-CH=CH_2 + CH_3CONH_2 + 2CO + H_2 \longrightarrow$$

$$CH_3-\overset{O}{\underset{OCH_3}{\overset{\|}{P}}}-CH_2CH_2\underset{NHCOCH_3}{CHCOOH}$$

Into a 100 ml stainless steel autoclave, 50 g of dioxane, 6.01 g (50 mmol) of vinylmethylphosphinic acid methyl ester, 3.55 g (60 mmol) of acetamide, 171 g (0.5 mmol) of dicobalt octacarbonyl and 5.4 mg (0.01 mmol) of hexarhodium hexacarbonyl were charged.

The autoclave was flushed with a gas mixture of carbon monoxide and hydrogen (1:1 in molar ratio), and the reaction was conducted at 80° C. under 120 kg/cm²G for one hour.

The autoclave was cooled, and the reaction product was taken out and analyzed by gas chromatography, whereby the conversion of the vinylmethylphosphinic acid methyl ester was 100%.

The solvent was distilled off, and the residue was repeatedly extracted with an organic solvent to obtain 12.41 g of a product. From the proton NMR analysis, this product was found to contain 70% by weight of desired N-acetyl-2-amino-4-methoxymethylphosphinylbutyric acid.

EXAMPLE 3

$$CH_3P\overset{O}{\underset{OCH_2CH_2Cl}{\overset{\|}{\diagup}}}\overset{CH=CH_2}{} + CH_3CONH_2 + 2CO + H_2 \longrightarrow$$

$$CH_3P\overset{O}{\underset{OCH_2CH_2Cl}{\overset{\|}{\diagup}}}\overset{CH_2CH_2\underset{|}{CHCOOH}}{\overset{NHCOCH_3}{}}$$

Into a 100 ml stainless steel autoclave, 51.7 g of dioxane, 5.06 g (30 mmol) of vinylmethylphosphinic acid 2-chloroethyl ester, 1.77 g (30 mmol) of acetamide and 103 mg (0.3 mmol) of dicobalt octacarbonyl were charged.

The autoclave was flushed with a gas mixture of hydrogen and carbon monoxide (1:1 in molar ratio), and the reaction was conducted at 100° C. under 200 kg/cm²G for 4 hours.

The autoclave was cooled, and the reaction product was taken out and analyzed by gas chromatography, whereby the conversion of the vinylmethylphosphinic acid 2-chloroethyl ester was 100%.

This reaction product was methylated with diazomethane and subjected to column chromatography separation, and the following analyses were applied to this product.

Mass spectrum: M/e 300 (M+H), 198(base peak).
$^{13}$CNMR(D$_2$O): δ (ppm) 13.6, 22.4, 24.1, 25.6, 42.9, 51.9, 52.1, 63.7, 170.4, 171.8.

From the above results and the results of the proton NMR analysis, this methylated product was found to be N-acetyl-2-amino-4-(2-chloroethoxy)methylphosphinylbutyric acid methyl ester.

Then, this methylated product was analyzed by gas chromatography, whereby the yield of N-acetyl-2-amino-4-(2-chloroethoxy)methylphosphinylbutyric acid was 82%.

EXAMPLE 4

The reaction and after-treatment were conducted in the same manner as in Example 3 except that 51.7 g of tetrahydrofuran was used instead of dioxane.

The conversion of the vinylmethyl phosphinic acid 2-chloroethyl ester was 100%, and the yield of N-acetyl-2-amino-4-(2-chloroethoxy)methylphosphinylbutyric acid was 83%.

EXAMPLE 5

The reaction and after-treatment were conducted in the same manner as in Example 3 except that the reaction was conducted at 80° C. under 200 kg/cm²G for 6 hours.

The conversion of the vinylmethylphosphinic acid 2-chloroethy ester was 100%, and the yield of N-acetyl-2-amino-4-(2-chloroethoxy)methylphosphinylbutyric acid was 73%.

EXAMPLE 6

The reaction and after-treatment were conducted in the same manner as in Example 3 except that 52 mg (0.15 mmol) of dicobalt octacarbonyl was used and the reaction was conducted at 100° C. under 200 kg/cm²G for 7 hours.

The conversion of the vinylmethylphosphinic acid 2-chloroethyl ester was 100%, and the yield of N-acetyl-2-amino-4-(2-chloroethoxy)methylphosphinylbutyric acid was 83%.

EXAMPLE 7

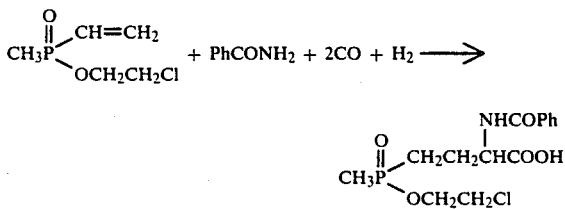

The reaction and after-treatment were conducted in the same manner as in Example 3 except that 3.63 g (30 mmol) of benzamide was used instead of acetamide and the reaction was conducted at 100° C. under 200 kg/cm²G for 6 hours.

The conversion of the vinylmethylphosphinic acid 2-chloroethyl ester was 97% and the yield of N-benzoyl-2-amino-4-(2-chloroethoxy)methylphosphinylbutyric acid was 40%.

EXAMPLE 8

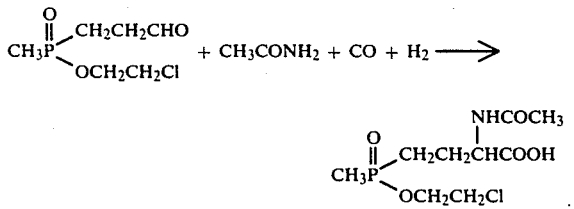

The reaction and after-treatment were conducted in the same manner as in Example 3 except that 5.94 g (30 mmol) of methyl(3-oxopropyl)phosphinic acid 2-chloroethyl ester was used instead of the vinylmethylphosphinic acid 2-chloroethyl ester. The conversion of the methyl(3-oxopropyl)phosphinic acid 2-chloroethyl ester was 100%, and the yield of N-benzoyl-2-amino-4-(2-chloroethoxy)methylphosphinylbutyric acid was 69%.

EXAMPLE 9

Into a 100 ml stainless steel autoclave, 51.7 g of dioxane, 5.06 g (30 mmol) of vinylmethylphosphinic acid 2-chloroethyl ester, 1.77 g (30 mmol) of acetamide and 103 mg of (0.3 mmol) of dicobalt octacarbonyl were charged.

The autoclave was flushed with a gas mixture of hydrogen and carbon monoxide (1:1 in molar ratio), and the reaction was conducted at 100° C. under 200 kg/cm²G for 4 hours.

This reaction product was treated as follows.

19 g of the reaction product and 0.5 ml of 20% hydrochloric acid were put into an Erlenmeyer flask and stirred at room temperature for 15 minutes while introducing air.

Then, after the recovery of the solvent dioxane, 100 ml of distilled water was added to the reaction mixture.

This aqueous solution was extracted with benzene to remove by-products.

After the extraction with benzene, this aqueous solution was passed through a column having an internal diameter of 30 mm and a length of 600 mm packed with 50 ml of a commercially available cation exchange resin (Lewatit 112, manufactured by Mitsuitoatsu Fine K.K.) which was pretreated to H-form by a usual method, at a flow rate of 100 ml/hr and then washed with 500 ml of deionized water. The eluted aqueous solution was collected. From this eluted aqueous solution, water was removed, and the residue was recrystallized from a solvent mixture of acetone/water to obtain 2.21 g of N-acetyl-2-amino-4-(2-chloroethoxy)methylphosphinylbutyric acid. Yield: 81.2%

This N-acetyl-2-amino-4-(2-chloroethoxy) methylphosphinylbutyric acid was subjected to atomic absorption analysis, whereby the content of cobalt metal was 1 ppm.

Separately, 19 g of the reaction product and 0.5 ml of 20% hydrochloric acid were put in an Erlenmeyer flask and stirred at room temperature for 15 minutes while introducing air to obtain an aqueous solution. This aqueous solution was recrystallized without subjecting to cation exchange resin treatment, whereby obtained N-acetyl-2-amino-4-(2-chloroethoxy)methylphosphinylbutyric acid was colored blue, and the content of cobalt metal was about 450 ppm.

We claim:

1. A process for producing a phosphinylamino acid derivative of the formula:

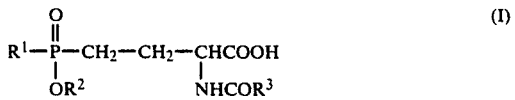

wherein R¹ is a lower alkyl group, R² is a hydrogen atom, a lower alkyl group, a halo-lower alkyl group or a substituted or unsubstituted phenyl group, and R³ is a substituted or unsubstituted alkyl group or a substituted or unsubstituted phenyl group, which comprises reacting a compound of the formula:

wherein R¹ and R² are as defined above, and/or a compound of the formula:

$$R^1-\overset{\overset{O}{\|}}{\underset{OR^2}{P}}-CH_2CH_2CHO \quad (III)$$

wherein $R^1$ and $R^2$ are as defined above, with a compound of the formula:

$$R^3COHN_2 \quad (IV)$$

wherein $R^3$ is as defined above, carbon monoxide and hydrogen in the presence of a catalyst containing a metal of Group VIII of the Periodic Table.

2. The process according to claim 1, wherein $R^1$ is a methyl group, $R^2$ is a hydrogen atom, a methyl group or a halogenoethyl group, and $R^3$ is a lower alkyl group or a phenyl group.

3. The process according to claim 1, wherein the reaction is conducted under a pressure of from 40 to 350 kg/cm$^2$G.

4. The process according to claim 1, wherein the reaction is conducted at a temperature of from 40° to 200° C.

5. The process according to claim 1, wherein the catalyst is a cobalt carbonyl compound and/or a rhodium carbonyl compound.

6. A process for producing a phosphinylamino acid derivative of the formula:

$$R^1-\overset{\overset{O}{\|}}{\underset{OR^2}{P}}-CH_2-CH_2-\underset{NHCOR^3}{CH}COOH \quad (I)$$

wherein $R^1$ is a lower alkyl group, $R^2$ is a hydrogen atom, a lower alkyl group, a halo-lower alkyl group or a substituted or unsubstituted phenyl group, and $R^3$ is a substituted or unsubstituted alkyl group or a substituted or unsubstituted phenyl group, which comprises reacting a compound of the formula:

$$R^1-\overset{\overset{O}{\|}}{\underset{OR^2}{P}}-CH=CH_2 \quad (II)$$

wherein $R^1$ and $R^2$ are as defined above, and/or a compound of the formula:

$$R^1-\overset{\overset{O}{\|}}{\underset{OR^2}{P}}-CH_2CH_2CHO \quad (III)$$

wherein $R^1$ and $R^2$ are as defined above, with a compound of the formula:

$$R^3CONH_2 \quad (IV)$$

wherein $R^3$ is as defined above, carbon monoxide and hydrogen in the presence of a catalyst containing a metal of Group VIII of the Periodic Table, and then separating the catalyst containing a Group VIII metal from the reaction solution by oxidizing the catalyst in the reaction solution in the presence of a mineral acid and adsorbing it on a cation exchange resin.

7. The process according to claim 6, wherein the mineral acid is hydrochloric acid or sulfuric acid.

8. The process according to claim 6, wherein the oxidation is conducted by an oxidizing agent selected from the group consisting of an oxygen-containing gas, chlorine or hydrogen peroxide.

9. The process according to claim 6, wherein the ctalyst containing a Group VIII metal is a cobalt carbonyl compound and/or a rhodium carbonyl compound.

* * * * *

UNITED STATES PATENT AND TRADEMARK OFFICE
CERTIFICATE OF CORRECTION

PATENT NO. : 4,906,764
DATED : March 6, 1990
INVENTOR(S) : HIDEKI TAKAMATSU ET AL It is certified that error appears in the above-identified patent and that said Letters Patent is hereby corrected as shown below:

Column 9, line 61: "N-benzoyl-" should read,

-- N-acetyl- --.

Signed and Sealed this

Twenty-third Day of April, 1991

Attest:

HARRY F. MANBECK, JR.

Attesting Officer

Commissioner of Patents and Trademarks